US007758854B2

(12) United States Patent
Filutowicz (10) Patent No.: US 7,758,854 B2
(45) Date of Patent: Jul. 20, 2010

(54) ANTI-MICROBIAL AGENTS (75) Inventor: Marcin S. Filutowicz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 787 days.

(21) Appl. No.: 10/250,645

(22) PCT Filed: Aug. 30, 2001

(86) PCT No.: PCT/US01/27028

§ 371 (c)(1),
(2), (4) Date: Jul. 3, 2003

(87) PCT Pub. No.: WO02/18605

PCT Pub. Date: Mar. 7, 2002

(65) Prior Publication Data

US 2004/0137002 A1  Jul. 15, 2004

(51) Int. Cl.
A61K 48/00 (2006.01)
A01N 63/00 (2006.01)
C12P 1/00 (2006.01)
C12P 39/00 (2006.01)
C12N 15/00 (2006.01)

(52) U.S. Cl. .................. 424/93.2; 424/93.4; 435/41; 435/42; 435/320.1

(58) Field of Classification Search .............. 424/93.2, 424/93.4; 435/41, 42, 320.1
See application file for complete search history.

(56) References Cited

U.S. PATENT DOCUMENTS

| 5,399,496 | A  | 3/1995  | Fujiwara et al. |
| 5,434,065 | A  | 7/1995  | Mahan et al. |
| 5,976,874 | A  | 11/1999 | Altman et al. |
| 6,019,984 | A  | 2/2000  | MacInnes et al. |
| 6,254,874 | B1 | 7/2001  | Mekalanos et al. |
| 6,716,631 | B1 | 4/2004  | delCardayre et al. |
| 6,780,405 | B1 | 8/2004  | Curtiss, III et al. |

FOREIGN PATENT DOCUMENTS

EP  0109150 A2  5/1984

OTHER PUBLICATIONS

Melcalf et al (Plasmid, 35, 1996,p. 1-7).*
Ambrozic et al, Microbiology (England), Feb. 1998, 144(Pt 2), p. 343-352).*
Roberts et al, (Journal of Bacteriology, Nov. 1990, 172 (11), p. 6204-6216).*
Klimke et al, (Journal of Bacteriology, Aug. 1998, 180 (16), p. 4036-4043).*
Rahal et al, (Annales de microbiologie (France), May-Jun. 1978, 129 (4), p. 409-414).*
Haugen et al (Plasmid 33, 27-39, 1995).*
Metcalf, Gene, 138, 1994, 1-7.*
Kaniga, et al., Gene 109, 1991, 137-141.
Ambrozic, Jerneja et al., *Escherichia coli* ColV plasmid pRK100: genetic organization, stability and conjugal transfer, Microbiology, Feb. 1998, 144 (Pt. 2), p. 343-352.
Blasina, A., et al., "Copy-up mutants of the plasmid RK2 replication initiation protein are defective in coupling RK2 replication origins," Proc. Natl. Acad. Sci. USA, Apr. 1996, 93, 3559-3564.
Diaz, E. et al., "Universal barrier to lateral spread of specific genes among microorganisms," Molecular Microbiology, XP 000579401, 1994, 13(5), 855-861.
Filutowicz, M. and Rakowski, S.A., Regulatory implications of protein assemblies at the γ origin of plasmid R6K—a review. Gene 223:195-204 (1998).
Haugan, K. et al., "The Host Range of RK2 Minimal Replicon Copy-Up Mutants Is Limited by Species-Specific Differences in the Maximum Tolerable Copy Number," Plasmid, 1995, 33, 27-39.
Klimke, William A. et al., Genetic Analysis fo the Role of the Transfer Gene, traN, of the F and R100-1 Plasmids in Mating Pair Stabilization during Conjugation, Journal of Bacteriology, Aug. 1998, 180 (16) p. 4036-4043.
Kudva, I.T. et al., Biocontrol of *Escherichia coli* O157 with O157-Specific Bacteriophages. Applied and Environmental Micorbiology 65:3767-3773 (1999).
Lessl, M. and Lanka, E., Common Mechanisms in Bacterial Conjugation and Ti-Mediated T-DNA Transfer to Plant Cells. Cell 77:321-324 (1994).
Metcalf et al, Conditionally Replicative and Conjugative Plasmids Carrying lacZα for Cloning, Mutagenesis, and Allele Replacement in Bacteria, Plasmid, 1996, 35, p. 1-13.
Molin, S. et al., Runaway Replication of Plasmid R1 Is Not Caused by Loss of Replication Inhibator Activity of Gene cop. Journal of Bacteriology 143:1046-1048 (1980).
Rahal et al, Annales de microbiologie, 1978, 129 (4), p. 409-414.
Reid, G., The Scientific Basis for Probiotic Strains of Lactobacillus. Applied and Environmental Microbiology 65:3763-3766 (1999).
Roberts, Richard C. et al., Genetic Characterization of the Stabilizing Functions of a Region of Broad-Host-Range Plasmid RK2. Journal of Bacteriology, vol. 172, No. 11, Nov. 1990, p. 6204-6216.
Rodriguez, M. et at., Lethality and Survival of *Klebsiella oxytoca* Evoked by.Conjugative IncN Group Plasmids. Journal of Bacteriology 177:6352-6361 (1995).
Smith, H.W. and Huggins, M.B., Successful Treatment of Experimental *Escherichia coli* Infections in Mice Using Phage: its General Superiority over Antibiotics. Journal of General Microbiology 128:307-318 (1982).
Smith, H.W. and Huggins, M.B., Effectiveness of Phages in Treating Experimental *Escherichia coli* Diarrhoea in Calves, Piglets and Lambs. Journal of General Microbiology 129:2659-2675 (1983).

(Continued)

*Primary Examiner*—Vanessa L. Ford
(74) *Attorney, Agent, or Firm*—Quarles & Brady, LLP (57) ABSTRACT Antimicrobial agents that can serve as replacements to conventional pharmaceutical antibiotics are disclosed. The antimicrobial agents comprise conjugatively transmissible plasmids that kill targeted pathogenic bacteria, but are not harmful to donor bacteria. Two types of lethal transmissible plasmids are disclosed. One type kills recipient bacteria by unchecked ("runaway") replication in the recipient cells and is prevented from occuring in donor cells. Another type kills recipient bacteria by expressing a gene that produces a product detrimental or lethal to recipient bacterial cells, that gene being prevented from expression in donor cells.

21 Claims, 3 Drawing Sheets

OTHER PUBLICATIONS

Smith, H.W. et al., The Control of Experimental *Escherichia coli* Diarrhoea in Calves by Means of Bacteriophages. Journal of General Microbiology 133:1111-1126 (1987).

Toukdarian, A.E. and Helsinki, D.R., TrfA dimers play a role in copy-number control of RK2 replication. Gene 223:205-211 (1998).

Horst Neve, et al. "Conjugal Transfer and characterization of bacteriocin Plasmids in Group N . . . ", Journal of Bacteriology, Mar. 1984, pp. 833-838, 157:3.

Del Solar et al., Microbiology and Molecular Biology Reviews, 1998, 434-464.

* cited by examiner

ANTI-MICROBIAL AGENTS

Pursuant to 35 U.S.C. §202(c), it is acknowledged that the United States government has certain rights in the invention described herein, which was made in part with finds from the National Institutes of Health, Grant No. GM40314.

This application claims priority to U.S. application Ser. No. 09/651,290, filed Aug. 30, 2000, the entirety of which is incorporated by reference herein.

FIELD OF THE INVENTION

The present invention relates to the field of bacteriology. In particular, the invention relates to novel antimicrobial agents comprising transmissible plasmids that kill targeted recipient bacteria, but are not harmful to donor bacteria.

BACKGROUND OF THE INVENTION

Various patents, patent publications and scientific articles are referenced in parentheses throughout the specification. These publications are incorporated by reference herein in their entireties.

As the use of conventional pharmaceutical antibiotics (herein referred to as antibiotics) increases for medical, veterinary and agricultural purposes, the increasing emergence of antibiotic-resistant strains of pathogenic bacteria is an unwelcome consequence. This has become of major concern inasmuch as drug resistance of bacterial pathogens is presently the major cause of failure in the treatment of infectious diseases. Indeed, people now die of certain bacterial infections that previously could have been easily treated with existing antibiotics. Such infections include, for instance, *Staphylococcus pneumoniae*, causing meningitis; Enterobacter sp., causing pneumonia; Enterococcus sp., cawing endocarditis, and *Mycobacterium tuberculosis*, causing tuberculosis.

The emergence of single- or multi-drug resistant bacteria results from a gene mobilization that responds quickly to the strong selective pressure that is a consequence of antibiotic uses. Over the last several decades, the increasingly frequent usage of antibiotics has acted in concert with spontaneous mutations arising in the bacterial gene pool to produce antibiotic resistance in certain strains. This gene pool is continually utilized by previously sensitive strains capable of accessing it by various means including the transfer of extrachromosomal elements (plasmids) by conjugation. As a result, single- and multi-drug resistance genes are commonly found in a large variety of bacterial plasmids.

Presently there is no known method by which to avoid the selection of antibiotic resistant bacterial mutants that arise as a result of the many standard applications of antibiotics in the modern world. Accordingly, a need exists to develop alternative strategies of antibacterial treatment.

Interest in the use of bacteriophages to treat infectious bacterial diseases developed early in the twentieth century, and has undergone a resurgence in recent years. For instance, bacteriophages have been shown effective in the treatment of certain pathogenic *E. coli* species in laboratory and farm animals, and have been proposed as a viable alternative to the use of antibiotics (Smith & Huggins, J. Gen. Microbiol. 128: 307-318, 1981; Smith & Huggins, J. Gen. Microbiol. 129: 2659-2675, 1983; Smith et al., J. Gem Microbiol. 133: 1111-1126, 1986; Kuvda et al., Appl. Env. Microbiol. 65: 3767-3773, 1999). However, the use of bacteriophages as antimicrobial agents has certain limitations. First, the relationship between a phage and its host bacterial cell is typically very specific, such that a broad host-range phage agent generally is unavailable. Second, the specificity of interaction usually arises at the point of the recognition and binding of phage to the host cell. This often occurs through the expression of surface receptors on the host cell to which a phage specifically binds. Inasmuch as such receptors are usually encoded by a single gene, mutations in the host bacterial cell to alter the surface receptor, thereby escaping detection by the phage, can occur with a frequency equivalent to or higher than, the mutation rate to acquire antibiotic resistance. As a result, if phage were utilized as commonly as antibiotics, resistance of pathogenic bacteria to phages could become as common a problem as antibiotic resistance.

Another approach to controlling pathogenic bacteria has been proposed, which relies on using molecular biological techniques to prevent the expression of antibiotic resistance genes in pathogenic bacteria (U.S. Pat. No. 5,976,864 to Altman et al.). In this method, a nucleic acid construct encoding an "external guide sequence" specific for the targeted antibiotic resistance gene is introduced into the pathogenic bacterial cells. The sequence is expressed, hybridizes with messenger RNA (mRNA) encoding the antibiotic resistance gene product, and renders such mRNA sensitive to cleavage by the enzyme RNAse P. Such a system also has limited utility, since it is targeted to specific antibiotic resistance genes. While the system may be effective in overcoming resistance based on expression of those specific genes, continued use of the antibiotics places selective pressure on the bacteria to mutate other genes and develop resistance to the antibiotic by another mechanism.

It is clear from the foregoing discussion that current alternatives to antibiotic use are limited and suffer many of the same drawbacks as antibiotic use itself. Thus, a need exists for a method of controlling unwanted bacteria that is flexible in range and that cannot be overcome by the bacteria by a single or small number of mutations.

SUMMARY OF THE INVENTION

The present invention provides novel antibacterial agents that are efficiently transferred to bacteria, e.g., pathogenic bacteria, that have a flexible range, and to which the target bacteria have difficulty developing resistance. These antibacterial agents offer an effective alternative to the use of conventional antibiotics. This invention relies on a universal property of conjugative systems whereby plasmid-encoded information, even that encoding self-destruction, will be expressed upon transfer to a recipient cell. That property was used to engineer a broad-host lethal system to limit the lateral spread of cloned genes (Diaz et al., 1994, Mol. Microbiol. 13, 855-861).

According to one aspect of the invention, an antibacterial agent is provided that comprises a donor cell, e.g., a non-pathogenic bacterial cell, harboring at least one transmissible plasmid having the following features: (a) an origin of replication for synthesizing the plasmid DNA in the donor cell, wherein initiation of replication at the origin of replication is negatively controlled by a plasmid replication repressor; (b) an origin of transfer to provide the initiation site for conjugative transfer of the transmissible plasmid from the donor cell to at least one recipient cell; and (c) at least one selectable marker gene. The donor cell further comprises one or more conjugative transfer genes conferring upon the donor cell the ability to conjugatively transfer the transmissible plasmid to the recipient cell. The donor cell also produces the plasmid replication repressor. In some embodiments, the recipient cell is a bacterium that does not produce the plasmid replication repressor. In preferred embodiments, the recipient cell is pathogenic.

According to another aspect of the invention, an antibacterial agent is provided which comprises a donor cell, e.g., a non-pathogenic bacterial cell, harboring at least one transmissible plasmid comprising the following features: (a) an origin of replication for synthesizing the plasmid DNA in the donor cell; (b) an origin of transfer to provide the start site for conjugative transfer of the transmissible plasmid from the donor cell to at least one recipient cell; and (c) at least one killer gene that, upon expression in a recipient cell, produces a product that kills the cell. The donor cell again comprises one or more transfer genes conferring upon the donor cell the ability to conjugatively transfer the transmissible plasmid to the recipient cell, and is modified so as to be unaffected by the product of the killer gene. In some embodiments, the recipient cell is a bacterium that is affected by the product of the killer gene. In preferred embodiments, the recipient cell is pathogenic.

The present invention also provides methods of treating a subject for a bacterial infection, which comprises administering to the subject one of the aforementioned antibacterial agents. A mode of administration is selected such that the donor cells of the antibacterial agent come into conjugative proximity to the unwanted recipient cells, such that the transmissible plasmids of the donor cells are conjugatively transferred from the donors to the unwanted recipient cells. In some embodiments, the transferred plasmid undergoes unchecked replication. In other embodiments, at least one killer gene is expressed to produce a gene product that is detrimental or lethal to the unwanted recipient cells.

The present invention also provides pharmaceutical preparations for treating a patient for a bacterial infection. These preparations comprise one of the aforementioned antibacterial agents, formulated for a pre-determined route of administration to the patient.

The present invention further provides methods of using the antibacterial agents of the invention in agricultural, veterinary, environmental and food maintenance applications. In these methods, the antibacterial agents of the invention are applied to (1) plant surfaces to reduce or prevent bacterial plant disease or spoilage, (2) food surfaces to reduce or prevent post harvest spoilage of vegetables, meat or fish, (3) animal feed to reduce the bio-burden. Other similar applications are also provided.

Other features and advantages of the present invention will be understood by reference to the drawings, detailed description and examples that follow.

DETAILED DESCRIPTION OF THE INVENTION

The present invention provides novel antibacterial strategies that utilize the highly efficient bacterial conjugation system to transfer a "killer" plasmid from a donor cell that is engineered to be resistant to the killer plasmid, to a target bacterial cell that is not.

In one aspect of the invention, the "killer plasmid" is one that undergoes runaway replication in the recipient cells, ultimately killing the cells. The basic principles underlying the mechanism by which runaway plasmid replication kills cells are outlined below.

Plasmids are generally dispensable DNA molecules that are stably maintained in bacterial populations. Plasmids replicate extra-chromosomally inside the bacterium and can transfer their DNA from one cell to another by a variety of mechanisms. DNA sequences controlling extra chromosomal replication (ori) and transfer (tra) are distinct from one another; i.e., a replication sequence generally does not control plasmid transfer, or vice-versa. Replication and transfer are both complex molecular processes that make use of both plasmid- and host-encoded functions.

Bacterial conjugation is the unidirectional and horizontal transmission of genetic information from one bacterium to another. The genetic material transferred may be a plasmid or it may be part of a chromosome. Bacterial cells possessing a conjugative plasmid contain a surface structure (the sex pilus) that is involved in the coupling of donor and recipient cells, and the transfer of the genetic information. Conjugation involves contact between cells, and the transfer of genetic traits can be mediated by many plasmids.

Among all natural transfer mechanisms, conjugation is the most efficient. For example, F plasmid of *E. coli*, pCF10 plasmid of *Enterococcus faecalis* and pXO16 plasmid of *Bacillus thuringiensis* employ different mechanisms for the establishment of mating pairs, the sizes of mating aggregates are different, and they have different host ranges within gram-negative (F) as well as gram-positive (pCF10 and pXO16) bacteria. Their plasmid sizes are also different; 54, 100 and 200 kb, respectively. Remarkably, however, those conjugation systems have very important characteristics in common: they are able to sustain conjugative transfer in liquid medium and transfer efficiencies close to 100% are often reached in a very short time (Dunny et al., 1982, J. Bacteriol. 151, 855-859; Andrup, et al., 1998, Plasmid 40, 30-43; Andrup L, and Andersen, K., 1999), Microbiology 145, 2001-2009; and Jansen et al., 1996, Curr. Microbiol. 33, 228-236. Thus, the conjugative process permits the protection of plasmid DNA against environmental nucleases, and the very efficient delivery of plasmid DNA into a recipient cell.

Conjugation functions are plasmid encoded. Numerous conjugative plasmids (and transposons) are known, which can transfer associated genes within one species (narrow host range) or between many species (broad host range). Transmissible plasmids have been reported in numerous Gram-positive genera, including but not limited to pathogenic strains of *Streptococcus, Staphylococcus, Bacillus, Clostridium* and *Nocardia*. The early stages of conjugation generally differ in Gram-negative and Gram-positive bacteria. The role of some of the transfer genes in conjugative plasmids from Gram-negative bacteria is to provide pilus-mediated cell-to-cell contact, formation of a conjugation pore and related morphological functions. The pili do not appear to be involved in initiating conjugation in Gram-positive bacteria The feature best understood in the Enterococci is the involvement of pheromones. Pheromones are hydrophobic polypeptides of 7-8 amino acids produced by potential recipient cells. Pheromones invite attention of potential donor cells containing conjugative plasmids. PAD1 is one of the best studied pheromone-induced plasmids which can replicate in 50 different bacterial hosts in addition to *Enterococcus faecelis* strains from which it was initially isolated (Clewell D. B. 1999. Sex pheromone systems in Enterococci, In: Cell-Cell Signaling in Bacteria, Ed. G. M. Dunny, S. C. Winans; ASM, Washington D.C. pp 47-65). Moreover, conjugation can occur between genera as widely diverse as anaerobes and aerobes.

Naturally occurring plasmids are present within host cells at a characteristic concentration (referred to herein as a particular plasmid "copy number"). Of great significance to the present invention is the fact that plasmid copy number is negatively controlled Helinski et al., 1996 (In *Escherichia coli and Salmonella Cellular and Molecular Biology*, Vol. 2 (ed F. Neidhardt, et al., 2295-2324, ASM Press, Washington D.C.). Thus, mutations that destroy the elements of the negative control cause an over-replication phenotype that manifests itself by an increase in the plasmid copy number ("copy-up" phenotype). In extreme cases of copy-up mutations, plasmid replication is completely unchecked due to the loss of copy control mechanisms. This is referred to as "runaway plasmid replication" or simply "runaway replication."

Runaway plasmid replication is lethal for the host cell. This is because, although the plasmid encodes the replication (Rep) protein that controls its copy number, all other replication proteins are encoded by chromosomal genes. These chromosomally encoded proteins assemble into a complex called a replisome. A typical bacterial cell possesses a small, fixed number of replisomes. Because both the chromosome and the plasmids require the same replisomes for DNA synthesis, an excess of plasmids acts like a trap to occupy all of the replisomes within the cell. This results in the inability of the chromosome to replicate, ultimately leading to the death of the cell.

The use of runaway replication plasmids as a means to kill recipient cells has a number of advantages over conventional antibiotic methodologies. One significant advantage is that, since the entire host replication machinery is targeted, multiple mutations would be required to avoid death by elevating the expression or activity of the replisome sub-assemblies. For instance, mutations in ten genes would be required just to increase the amount or activity of DNA polymerase III holoenzyme (composed of ten different subunits), and this polymerase is just one of the replisome sub-assemblies. Thus, there is little or no chance of a bacterium acquiring resistance to being killed by over-replicating plasmids. In contrast, conventional antibiotics typically inhibit only a single enzymatic activity that is essential for the survival of a cell. A single-target strategy and the relatively high spontaneous mutation frequency for one gene ($10^{-6}$ to $10^{-8}$) unavoidably leads to the quick acquisition of resistance to such drugs.

Because runaway replication mutations are lethal to the host cell, the donor cells that maintain such plasmids are generally engineered so that replication of the plasmid is controlled e.g., by providing a wild-type Rep protein to the host cell. In some embodiments, this is accomplished by providing a Rep gene on another plasmid. In other embodiments, a rep gene is provided by integration into the bacterial chromosome of a donor cell using standard homologous recombination techniques.

In some embodiments, the antimicrobial strategy of the present invention comprises:
(1) a plasmid that, alone or with the assistance of a helper plasmid, comprises the genes necessary to effect conjugative transfer of the plasmid from a donor cell to a recipient cell, wherein replication of the plasmid is controlled, e.g., repressed, by a reversible mechanism, such as control by a product of a gene that can be de-activated (e.g., via mutation) so as to release the control on plasmid replication (referred to herein as a "runaway replication plasmid");
(2) a source of conjugative transfer genes (e.g. on the runaway replication plasmid, or on a separate "helper" plasmid); and
(3) a donor cell for maintaining the runaway replication plasmid in a replication-suppressed state, so as not to be killed by the plasmid.

A number of plasmids have been well characterized, and can serve as subjects for mutagenesis to create runaway mutants, which may be used in embodiments of the present invention Such mutant plasmids contain, or can be easily modified to contain all components needed for conjugative transfer from donor to recipient cells but are defective in their replicative repressor (Rep) function. Examples of such mutants, both broad-range and narrow-range, are known in the art (Haugan et al., Plasmid 33: 27-39, 1995; Molin et al., J. Bacteriol. 143: 1046-1048, 1980; Toukdarian & Helinski, Gene 223: 205-211, 1998). A particularly preferred plasmid of this type is a mutant of plasmid R6K, as described in detail in Examples 1 and 2. Other examples include, but are not limited to, RK2, pCU1, p15A, pIP501, pAMβ1 and pCRG1600.

As an alternative to the use of mutants, it may sometimes be preferable to use various components of conjugative plasmids whose features are well understood, to create plasmids having all necessary features. Such runaway replication plasmids or helper plasmids may include (1) an origin of replication (e.g., oriV as decribed herein), a sequence from which replication of the plasmid originates and the sequence that may be negatively regulated by a Rep protein; (2) an origin of transfer (e.g., oriT as described herein), a sequence from which a conjugal plasmid transfer originates; (3) transfer (tra) genes to effect conjugation; and (4) a screenable/selectable marker gene. The donor cell containing the runaway replication plasmid is engineered to contain a functional repressor (Rep) of replication at oriV, thereby controlling replication of the runaway replication plasmid while it is still in the donor.

Non-self-transmissible plasmid systems and self-transmissible plasmid systems are contemplated. Examples of these are shown schematically in FIGS. 2A and 2B. The systems diagrammed here and described below are provided as examples of the systems of the present invention and are not to be construed as limiting the components or sources of components assembled to effect the methods and compositions of the invention. For example, where particular genes or genetic elements providing particular functions are named, (e.g., the oriV origin of replication, the oriT origin of transfer), it is contemplated that other genes or genetic elements providing equivalent functions or functional combinations may be used.

Figure 1:
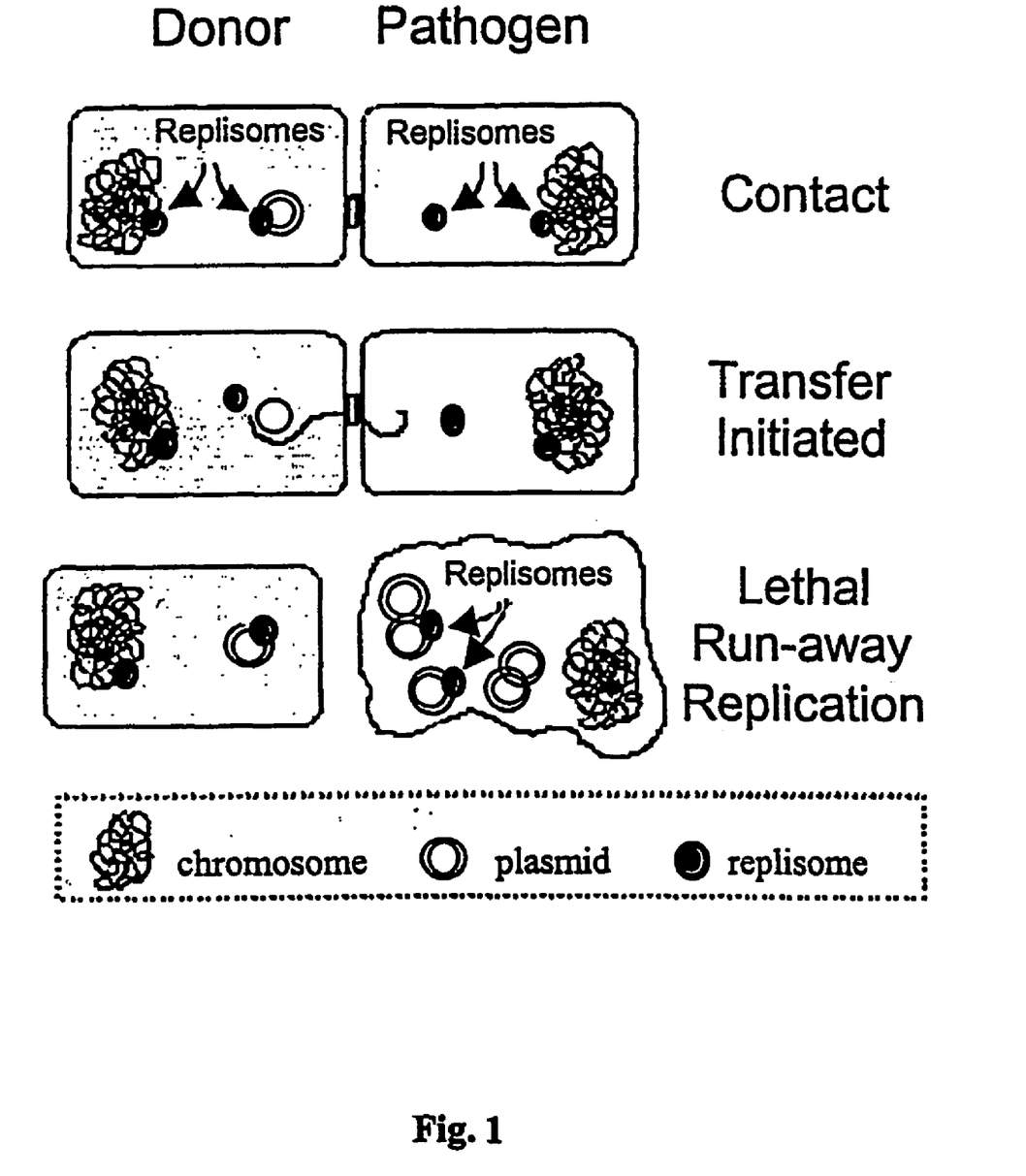
FIG. 1. Schematic diagram showing a process of killing bacteria by conjugative transfer of plasmids that engage in runaway replication in the recipient cells.
Figure 2A:
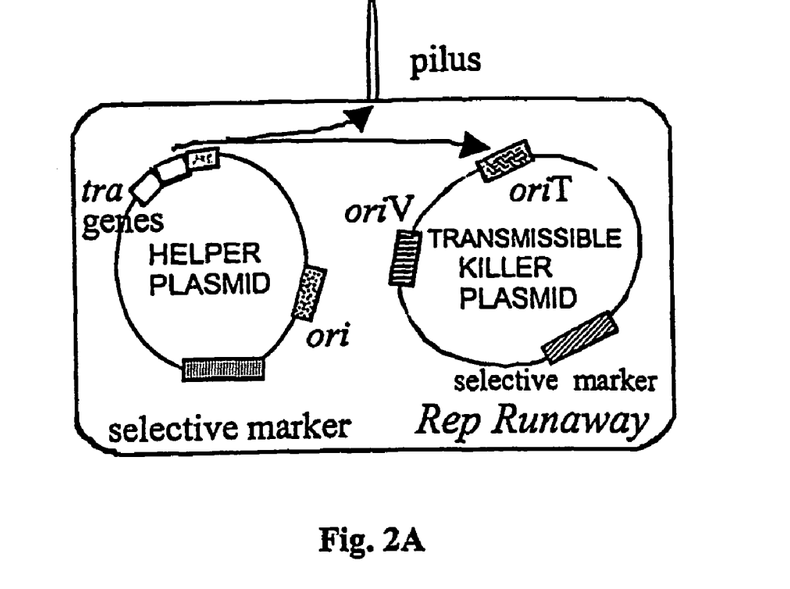
FIG. 2A. Schematic diagram of a non-self-transmissible, runaway replication plasmid system using a helper plasmid and a transmissible runaway replication plasmid.

In some embodiments of non-self-transmissible systems (e.g., as shown in FIG. 2A), the runaway replication plasmid contains an oriT, an oriV and a selectable marker gene. In some embodiments, a helper plasmid contains the additional tra genes, along with its own origin of replication and a selective marker. Thus, the helper plasmid enables conjugative transfer of the runaway replication plasmid, but is itself confined to the donor cell due to its lack of an oriT. In other embodiments, the tra genes are integrated into the chromosome of the donor cell. Since the runaway replication plasmid lacks the necessary tra genes to convert the recipient cell into a donor cell, the cycle of conjugation ends with the original recipient cell. It cannot transfer its runaway replication plasmid to a second recipient before it dies.

Figure 2B:
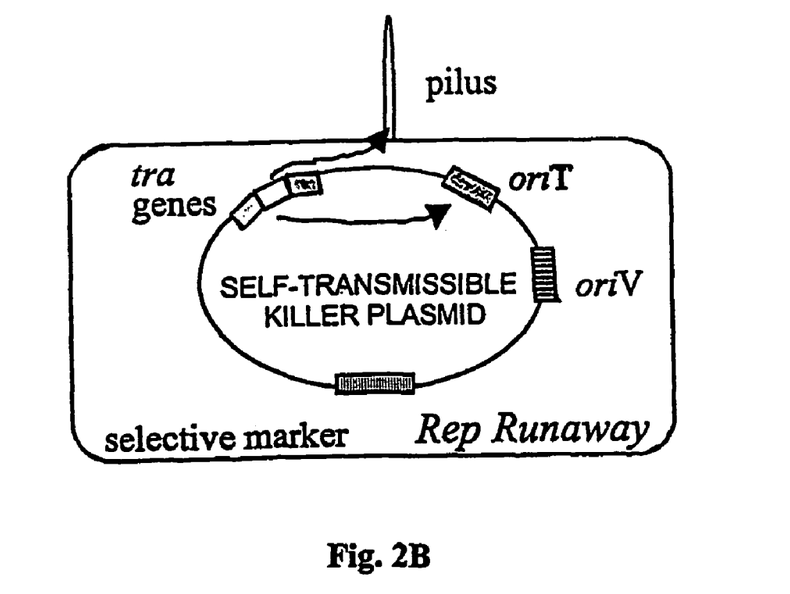
FIG. 2B. Schematic diagram of a self-transmissible, runaway replication plasmid system.

In some embodiments of self-transmissible systems (e.g., as shown in FIG. 2B), the runaway replication plasmid contains an oriT, an oriV and a selectable marker gene. It also contains the additional tra genes needed for conjugative transfer. Thus, unlike the non-self-transmissible plasmid described above, once this plasmid has been transmitted from the original donor to a first recipient, it is capable of transmitting itself again to subsequent recipients before the first recipient cell is killed by runaway replication. A plasmid of this type has the capability of much faster dissemination among recipient cells than the non-self-transmissible type, resulting in faster and more widespread killing of those cells.

In either the self-transmissible or the self-non-transmissible system, the donor cells generally comprise a means of controlling plasmid replication. In some embodiments, the control comprises a gene encoding a repressor of plasmid replication. For example, the Rep protein represses plasmid replication initiated at oriV. In some embodiments, a Rep-encoding gene is provided on a helper plasmid. In other embodiments, a Rep-encoding gene is integrated into the donor cell chromosomal DNA. Plasmid DNA comprising the Rep-encoding gene may be introduced into bacterial cells by any commonly known technique (e.g., transformation). The Rep-encoding gene can be integrated into the host genome by a site-specific recombination, according to standard methods (Li-Ch Huang, E. Wood and M. Cox; J. Bacteriol. 179: 6076-6083, 1997).

A number of bacterial oriV's and the Rep proteins that negatively control them have been characterized. Each of these is contemplated for use in the present invention. Examples of suitable oriV/Rep systems for use in the invention include, but are not limited to: RK2, R6K, rts 1, p15A, RSF1010, F and P1. A wide variety of replication systems may be used in the present invention (see, e.g., U.S. Pat. No. 5,851,808). The present invention is not limited to those systems described above.

The selection of oriV will confer on the system its range of potential recipients for runaway replicating plasmids. In most instances it may be preferable to target a specific recipient of the runaway replication plasmid. Such instances include, but are not limited to using the conjugative runaway plasmids for combating Enterobacteria, Enterococci, Staphylococci and non-sporulating Gram-positive pathogens such as Nocardia and Mycobacterium sp. Examples of selective host range plasmids from which such oriV's may be obtained include, but are not limited to, P1 and F.

In instances where it is desirable to affect a wide variety of recipients, a broad range oriV is employed. Examples of broad range ("promiscuous") plasmids from which oriVs may be obtained include, but are not limited to: R6K, RK2, p15A and RSF1010.

As used herein, the term "range" (or "host range") refers generally to parameters of both the number and diversity of different bacterial species in which a particular plasmid (natural or recombinant) can replicate. Of these two parameters, one skilled in the art would consider diversity of organisms as generally more defining of host range. For instance, if a plasmid replicates in many species of one group, e.g., Enterobacteriaceae, it may be considered to be of narrow host range. By comparison, if a plasmid is reported to replicate in only a few species, but those species are from phylogenetically diverse groups, that plasmid may be considered of broad host range. As discussed above, both types of plasmids (or components thereof) will find utility in the present invention.

Conjugative transfer (tra) genes also have been characterized in many conjugative bacterial plasmids. The interchangeability between the gene modules conferring the ranges of hosts susceptible for conjugal transfer and vegetative replication include Gram-positive and Gram-negative species. Examples of characterized tra genes that are suitable for use in the present invention are the tra genes from: (1) F (Firth, N., Ippen-Ihler, K. and Skurray, R. A. 1996, Structure and function of F factor and mechanism of conjugation. In: *Escherichia coli* and Salmonella, Neidhard et al., eds., ASM Press, Washington D.C.); (2) R6K (Nunez et al., Mol. Microbiol. 24: 1157-1168, 1997); and (3) Ti (Ferrand et al., J. Bacteriol. 178: 4233-4247, 1996). Additional tra genes that find use with the present invention include, but are not limited to, those described in U.S. Pat. Nos. 6,180,406 and 6,251,674.

According to another aspect of the invention, the bacterial conjugation system is again utilized, this time to efficiently deliver a variety of "killer genes" to target bacterial cells. The delivery of various killer genes to bacterial cells occurs in nature, upon infection of bacteria with bacteriophages. Bacteriophages utilize a number of different mechanisms to maintain their own replication cycles, generally resulting in lysis of the host bacterial cells. Indeed, bacteriophages have been proposed and used as alternatives to antibiotics, as discussed above in the Background of the Invention. One serious drawback to the use of bacteriophages for this purpose is that they are often extremely host-specific, binding only to cell surfaces possessing specific receptors. As a result, bacteria quickly develop resistance mutations in the receptor, thereby escaping recognition by the phage. The present invention circumvents that drawback by placing one or more killer genes (e.g., from a phage or other source) on a conjugative plasmid. The conjugative plasmid containing the killer gene(s), like the conjugative runaway replication plasmids described above, is thereafter efficiently distributed to recipient cells, killing them shortly thereafter. Additional killing systems include, but are not limited to, those described in U.S. Pat. No. 6,277,608.

Bacteriophages kill host cells by a variety of mechanisms, many of which are encoded by a discrete set of genes in the phage genome. For instance, bacteriophage MS2 contains a gene encoding a bacterial lysis protein (Coleman et al., J. Bacteriol. 153:1098-1100,1983). Phage T4D contains genes encoding proteins that degrade cytosine-containing DNA in bacterial host cells (Kutter and Wilberg, J. Mol. Biol. 38:395-411,1968). Other T4phages encode gene products that interfere with transcription of cytosine-containing DNA (Drivdahl and Kutter, J.Bacteriol. 172:2716-2727,1990). Yet other T4 gene products are responsible for the disruption of the bacterial nucleoid (Bouet et al., Gene 141:9-16,1994). Over 5000 characterized bacteriophages provide enormous reservoir of killer genes (Ackermann 2001. Arch. Vir., 146,843-857). Such killer genes can be inserted into a conjugative plasmid such as those described above, for efficient distribution to target recipient cells.

In addition, other types of killer genes may be utilized similarly. These include naturally-occurring or synthetic genes. A nonlimiting example of a naturally-occurring gene that is suitable for use in the invention is the hok gene product described by Gerdes et al. (EMBO J. 5: 2023-2029, 1986). Examples of man-made nucleic acid molecules that may be used in this aspect of the invention include: (1) sequences encoding peptides with bactericidal activity and endotoxin neutralizing activity for Gram-negative bacteria as described in U.S. Pat. No. 5,830,860; (2) sequences encoding RNA molecules with binding affinity to critical bacterial cellular targets (e.g., Chen and Gold, Biochemistry 33: 8746-8756, 1994); and (3) oligonucleotides generated by the SELEX method for the in vitro evolution of nucleic acid molecules with highly specific binding to target molecules as described in U.S. Pat. No. 5,475,096 and U.S. Pat No. 5,270,163.

Figure 3:
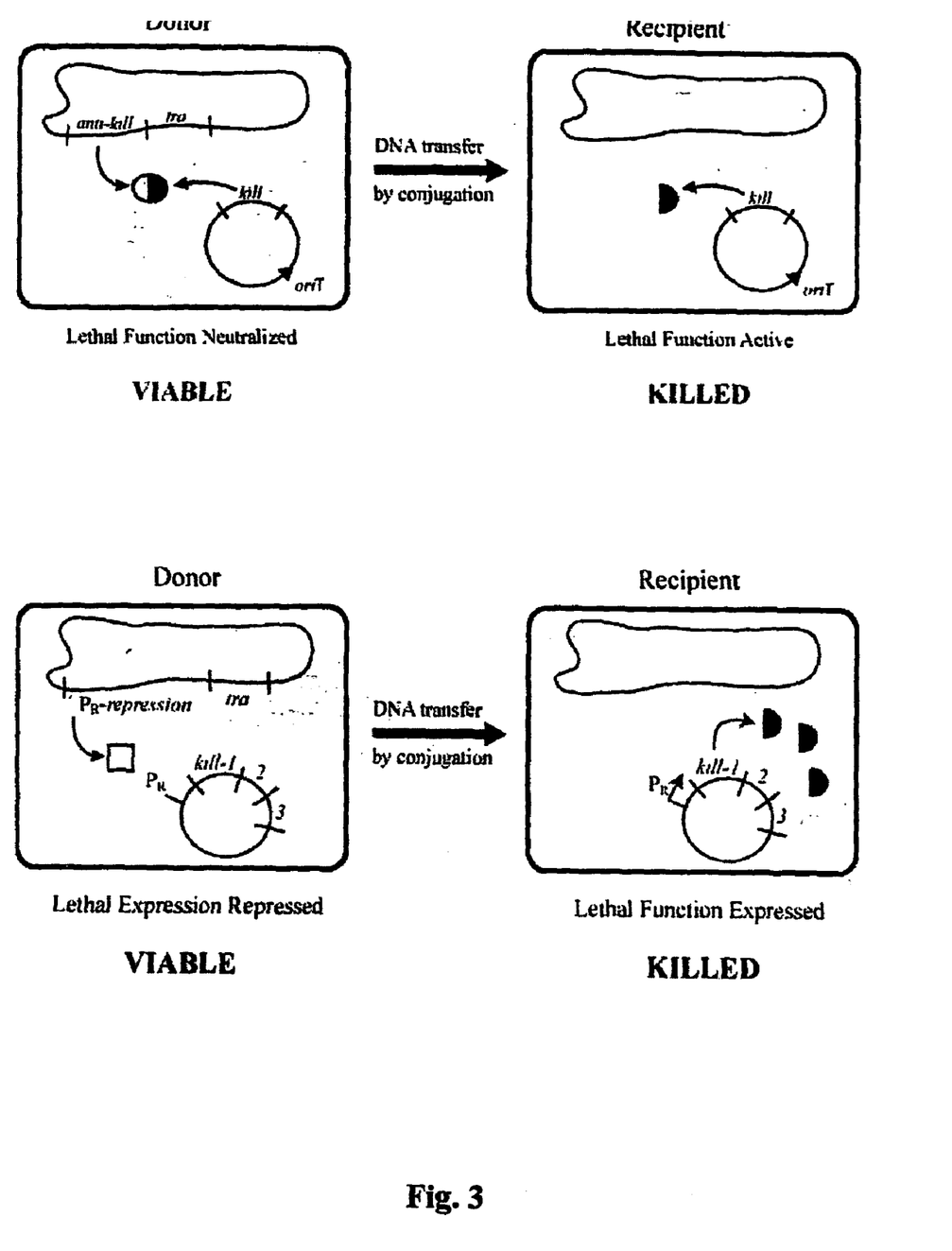
FIG. 3. Schematic diagrams showing a "Trojan-Horse"-like process of killing bacteria by conjugative transfer of plasmids that encode a kill product that is neutralized by an anti-kill product in the donor but is not neutralized in the recipient that lacks anti-kill gene as part of its chromosome (top). Bottom diagram represents a general scenario of process of killing bacteria by conjugatively transferred plasmid that contains a synthetically assembled operon that encodes one or more kill products. Expression of the operon is repressed in the donor but not in the recipient. The kill gene products can be either natural or man-made peptides or RNA.

In these systems, steps may be employed to prevent death of the donor cell For example, the death of the donor cell can be prevented by employing a synthetic promoter-operator system whose expression is prevented by the repressor made only in the donor cells (FIG. 3 bottom). In other embodiments, the toxin can be neutralized by an antitoxin made in donor but not in recipient bacteria (FIG. 3 top).

In preferred embodiments, the plasmid contains a screenable or selectable marker gene. In traditional molecular biological manipulations of recombinant bacteria, the selectable marker gene is an antibiotic resistance gene. Since the present invention is designed to avoid further spread of antibiotic resistance, an alternative selectable marker system is preferred for use in the present invention. Accordingly, though antibiotic resistance markers can be used in laboratory tests, preferred selectable markers are nutritional markers, i.e., any auxotrophic strain (e.g., $Trp^-$, $Leu^-$, $Pro^-$) containing a plasmid that carries a complementing gene (e.g., $trp^+$, $leu^+$, $pro^+$).

The donor bacterial strain for any of the above-described killer plasmids can be any one of thousands of free-living bacteria, associated with the body of warm-blooded animals, including humansand plants. Preferably, non-pathogenic bacteria that colonize the non-sterile parts of the body (e.g., skin, digestive tract, urogenital region, mouth, nasal passages, throat and upper airway, ears and eyes) are utilized as donor cells, and the methodology of the invention is used to combat bacterial infections of these parts of the body. In another embodiment, safe donors of these plasmids are developed for combating systemic infection. Examples of particularly preferred donor bacterial species include, but are not limited to: (1) non-pathogenic strains of *Escherichia coli* (*E. coli* F18 and *E. coli* strain Nissle 1917), (2) various species of *Lactobacillus* (such as *L. casei, L. plantarum, L. paracasei, L. acidophilus, L. fernentum, L. zeae* and *L. gasseri*), (3) other nonpathogenic or probiotic skin-or GI colonizing bacteria such as Lactococcus, Bifidobacteria, Eubacteria, and (4) bacterial mini-cells, which are anucleoid cells destined to die but still capable of transferring plasmids (see; e.g., Adler et al., Proc. Natl. Acad. Sci. USA 57; 321-326, 1970; Frazer and Curtiss III, Current Topics in Microbiology and Immunology 69: 1-84, 1975; U.S. Pat. No. 4,968,619 to Curtiss III).

In some embodiments, the target recipient cells are pathogenic bacteria dispersed throughout the body, but particularly on the skin or in the digestive tract, urogenital region, mouth, nasal passages, throat and upper airways, eyes and ears. Of particular interest for targeting and eradication are pathogenic strains of *Pseudomonasaeruginosa, Escherichia coli, Staphylococcus pneumoniae* and other species, *Enterobacter spp., Enterococcus spp.* and *Mycobacterium tuberculosis*. The present invention finds use with a wide array of target organisms (e.g., pathogenic organisms), whether in therapeutic, agricultural, or other settings, including, but not limited to, those described in U.S. Pat. Nos. 6,271,359, 6,261,842, 6,221,582, 6,153,381, 6,106,854, and 5,627,275. Others are also discussed herein, and still others will be readily apparent to those of skill in the art.

It is clear from the foregoing discussion that numerous types of killer plasmids (e.g., runaway replication plasmids, plasmids carrying lethal phage genes, etc.) are suitable for use in the present invention. In view of this, one of skill in the art will appreciate that a single donor bacterial strain might harbor more than one type of killer plasmid (e.g., runaway or toxin-producing). In other embodiments, a donor cell may harbor a killer plasmid expressing multiple kill functions, as shown in FIG. 3 (bottom) or may harbor multiple killer plasmids each expressing kill function(s) independently of the other plasmids. Thus such multiple plasmid systems can contain a plurality of plasmid-encoded functions targeted to different recipient cells. Further, two or more donor bacterial strains, each containing one or more killer plasmids, may be combined for a similar multi-target effect.

The systems of the present invention find utility for treatment of humans and in a variety of veterinary, agronomic, horticultural and food processing applications. For human and veterinary use, and depending on the cell population or tissue targeted for protection, the following modes of administration of the bacteria of the invention are contemplated: topical, oral, nasal, pulmonary/bronchial (e.g., via an inhaler), ophthalmic, rectal, urogenital, subcutaneous, intraperitoneal and intravenous. The bacteria preferably are supplied as a pharmaceutical preparation, in a delivery vehicle suitable for the mode of administration selected for the patient being treated. The term "patient" or "subject" as used herein refers to humans or animals (animals being particularly useful as models for clinical efficacy of a particular donor strain).

For instance, to deliver the bacteria to the gastrointestinal tract or to the nasal passages, the preferred mode of administration is by oral ingestion or nasal aerosol, or by feeding (alone or incorporated into the subject's feed or food). In this regard, it should be noted that probiotic bacteria, such as *Lactobacillus acidophilus*, are sold as gel capsules containing a lyophilized mixture of bacterial cells and a solid support such as mannitol. When the gel capsule is ingested with liquid, the lyophilized cells are re-hydrated and become viable, colonogenic bacteria. Thus, in a similar fashion, donor bacterial cells of the present invention can be supplied as a powdered, lyophilized preparation in a gel capsule, or in bulk for sprinkling into food or beverages. The re-hydrated, viable bacterial cells will then populate and/or colonize sites throughout the upper and lower gastrointestinal system, and thereafter come into contact with the target pathogenic bacteria.

For topical applications, the bacteria may be formulated as an ointment or cream to be spread on the affected skin surface. Ointment or cream formulations are also suitable for rectal or vaginal delivery, along with other standard formulations, such as suppositories. The appropriate formulations for topical, vaginal or rectal administration are well known to medicinal chemists.

The present invention will be of particular utility for topical or mucosal administrations to treat a variety of bacterial infections or bacterially related undesirable conditions. Some representative examples of these uses include treatment of (1) conjunctivitis, caused by *Haemophilus sp.*, and corneal ulcers, caused by *Pseudomonas aeruginosa*; (2) otititis externa, caused by *Pseudomonas aeruginosa*; (3) chronic sinusitis, caused by many Gram-positive cocci and Gram-negative rods, and for general decontamination of bronchii; (4) cystic fibrosis, associated with *Pseudomonas aeruginosa*; (5) enteritis, caused by *Helicobacter pylori* (ulcers), *Escherichia coli, Salmonella typhimurium*, Campylobacter and *Shigella sp.*; (6) open wounds, both surgical and non-surgical, as a prophylactic measure for many species; (7) burns to eliminate *Pseudomonas aeruginosa* or other Gram-negative pathogens; (8) acne, caused by *Propionobacter acnes*; (9) nose and 
skin infections caused by methicillin resistant *Staphylococcus aureus* (MSRA); (10) body odor caused mainly by Gram-positive anaerobic bacteria (i.e., use in deodorants); (11) bacterial vaginosis associated with *Gardnerella vaginalis* and other anaerobes; and (12) gingivitis and/or tooth decay caused by various organisms.

In other embodiments, the antimicrobials of the present invention find application in the treatment of surfaces for the removal or attenuation of unwanted bacterial. For example, surfaces that may be used in invasive treatments such as surgery, catheterization and the like may be treated to prevent infection of a subject by bacterial contaminants on the surface. It is contemplated that the methods and compositions of the present invention may be used to treat numerous surfaces, objects, materials and the like (e.g., medical or first aid equipment, nursery and kitchen equipment and surfaces) to control bacterial contamination thereon.

Pharmaceutical preparations comprising the donor bacteria are formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of the donor bacteria calculated to produce the desired antibacterial effect in association with the selected pharmaceutical carrier. Procedures for determining the appropriate dosage unit are well known to those skilled in the art.

Dosage units may be proportionately increased or decreased based on the weight of the patient. Appropriate concentrations for achieving eradication of pathogenic bacteria in a target cell population or tissue may be determined by dosage concentration curve calculations, as known in the art.

Other uses for the donor bacteria of the invention are also contemplated. These include a variety agricultural, horticultural, environmental and food processing applications. For example, in agriculture and horticulture, various plant pathogenic bacteria may be targeted in order to minimize plant disease. One example of a plant pathogen suitable for targeting is *Erwinia amylovora*, the causal agent of fire blight. Similar strategies may be utilized to reduce or prevent wilting of cut flowers.

In veterinary or animal agriculture, the killer plasmid systems of the invention may be incorporated into animal feed (chicken, cattle) to reduce bio-burden or to eliminate certain pathogenic organisms (e.g., *Salmonella*). In other embodiments, the invention may be utilized on meat or other foods to eliminate unwanted or pathogenic bacteria (e.g., *E. coli* O157:H7 on meat, or *Proteus* spp., one cause of "fishy odor" on seafood).

Environmental utilities comprise, for example, engineering *Bacillus thurengiensis* and one of its conjugative plasmids to deliver and conditionally express insecticidal agents (e.g., for the control of mosquitos that disseminate malaria or West Nile virus). In such applications, as well as in the agricultural and horticultural applications described above, formulation of the killer plasmids and donor bacteria as solutions, aerosols, or gel capsules are contemplated.

In preferred embodiments of the present invention, certain features are employed in the plasmids and donor cells of the invention to minimize potential risks associated with the use of DNA or genetically modified organisms in the environment. For instance, in environmentally sensitive circumstances it is preferable to utilize non-self-transmissible plasmids. Instead, the plasmids will be mobilizable by conjugative machinery but will not be self-transmissible. As discussed hereinabove, this may be accomplished in some embodiments by integrating into the host chromosome all tra genes whose products are necessary for the assembly of conjugative machinery. In such embodiments, killer plasmids are configured to possess only an origin of transfer (oriT). This feature prevents the recipient, before or even after it dies, from transferring the killer plasmid further.

Another biosafety feature comprises utilizing conjugation systems with pre-determined host-ranges. As discussed above, certain elements are known to function only in few related bacteria (narrow-host-range) and others are known to function in many unrelated bacteria (broad-host-range or promiscuous) (del Solar et al., Mol. Microbiol. 32:661-666, 1996; Zatyka and Thomas, FEMS Microbiol. Rev. 21:291-319, 1998). Also, many of those conjugation systems can function in either gram-positive or gram-negative bacteria but generally not in both (del Solar, 1996, supra; Zatyka and Thomas, 1998, supra).

Also as discussed in detail above, inadvertant proliferation of antibiotic resistance is minimized in this invention by avoiding the use of antibiotic resistance markers. In a preferred alternative approach, the gene responsible for the synthesis of an amino acid (i.e. serine) can be mutated, generating the requirement for this amino acid in the donor. Such mutant bacteria will prosper on media lacking serine provided that they contain a plasmid with the ser gene whose product is needed for growth: Thus, the invention contemplates the advantageous use of plasmids containing the ser gene or one of many other nutritional genetic markers. These markers will permit selection and maintenance of the killer plasmids in donor cells.

Another biosafety approach comprises the use of restriction-modification systems to modulate the host range of killer plasmids. Conjugation and plasmid establishment are expected to occur more frequently between taxonomically related species in which plasmid can evade restriction systems and replicate. Type II restriction endonucleases make a double-strand break within or near a specific recognition sequence of duplex DNA. Cognate modification enzymes can methylate the same sequence and protect it from cleavage. Restriction-modification systems (RM) are ubiquitous in bacteria and archaebacteria but are absent in eukaryotes. Some of RM systems are plasmid-encoded, while others are on the bacterial chromosome (Roberts and Macelis, Nucl. Acids Res. 24: 223-235, 1998). Restriction enzymes cleave foreign DNA such as viral or plasmid DNA when this DNA has not been modified by the appropriate modification enzyme. In this way, cells are protected from invasion of foreign DNA. Thus, by using a donor strain producing one or more methylases, cleavage by one or more restriction enzymes could be evaded. Site-directed mutagenesis is used to produce plasmid DNA that is either devoid of specific restriction sites or that comprises new sites, protecting or making plasmid DNA vulnerable, respectively against endonucleases. Broad-host range plasmids (eg. RP4) may evade restriction systems simply by not having many of the restriction cleavage sites that are typically present on narrow-host plasmids (Willkins et al., 1996, J. Mol. Biol 258, 447-456).

Preferred embodiments of the present invention also utilize environmentally safe bacteria as donors. For example, delivery of DNA vaccines by attenuated intracellular gram-positive and gram-negative bacteria has been reported (Dietrich et al., 2001 Vaccine 19, 2506-2512; Grillot-Courvalin et al., 1999 Current Opinion in Biotech 10, 477-481). In addition, the donor stain can be one of thousands of harmless bacteria that colonize the non-sterile parts of the body (e.g., skin, gastrointestinal, urogenital, mouth, nasal passages, throat and upper airway systems). Examples of preferred donor bacterial species are set forth hereinabove.

In another strategy, non-dividing, non-growing donors are utilized instead of living cells. As discussed above, minicells and maxicells are well studied model systems of metabolically active but nonviable bacterial cells. Minicells lack chromosomal DNA and are generated by special mutant cells that undergo cell division without DNA replication. If the cell contains a multicopy plasmid, many of the minicells will contain plasmids. Minicells neither divide nor grow. However, minicells that possess conjugative plasmids are capable of conjugal replication and transfer of plasmid DNA to living recipient cells. (Adler et al., 1970, supra; Frazer and Curtiss, 1975, supra; U.S. Pat. No. 4,968,619, supra).

Maxicells can be obtained from a strain of *E. coli* that carries mutations in the key DNA repair pathways (recA, uvrA and phr). Because maxicells lack so many DNA repair functions, they die upon exposure to low doses of UV. Importantly, plasmid molecules (e.g., pBR322) that do not receive an UV hit continue to replicate. Transcription and translation (plasmid-directed) can occur efficiently under such conditions (Sancar et al., J. Bacteriol. 137: 692-693, 1979), and the proteins made prior to irradiation should be sufficient to sustain conjugation. This is supported by the following two observations: i) that streptomycin-killed cells remain active donors, and ii) that transfer of conjugative plasmids can occur in the presence of antibiotics that prevent de novo gene expression (Heineman and Ankenbauer, 1993, J. Bacteriol. 175, 583-588; Cooper and Heineman, 2000. Plasmid 43, 171-175). Accordingly, UV-treated maxicells will be able to transfer plasmid DNA to live recipients. It should also be noted that the conservation of recA and uvrA genes among bacteria should allow maxicells of donor strains other than *E. coli* to be obtained.

Also contemplated for use in the invention are any of the modified microorganisms that cannot function because they contain temperature-sensitive mutation(s) in genes that encode for essential cellular functions (e.g., cell wall, protein synthesis, RNA synthesis, as described, for example, in U.S. Pat. No. 4,968,619, supra). For many approaches, conditionally replicating killer plasmids can be used. Such plasmids, which have been produced in accordance with the invention, can replicate in the donor but cannot replicate in the recipient bacterium simply because their cognate replication initiator protein (e.g., Rep) is produced in the former cells but not the latter cells. Another variant plasmid contains a temperature-sensitive mutation in the mentioned above rep gene, so it can replicate only at temperatures below 37° C. Hence, its replication will occur in bacteria applied on skin but it will not occur if such bacteria break into the body's core.

As used herein, the term "donor cell" refers to any of the above-listed cells, including dividing and non-dividing bacterial cells (minicells and maxicells), as well as conditionally non-functional cells.

The following examples are set forth to describe the invention in greater detail. They are intended to illustrate, not to limit, the invention. Unless otherwise specified, general cloning, microbiological, biochemical and molecular biological procedures such as those set forth in Sambrook et al., *Molecular Cloning*, Cold Spring Harbor Laboratory (1989) ("Sambrook et al.") or Ausubel et al. (eds) *Current Protocols in Molecular Biology*. John Wiley & Sons (2001) ("Ausubel et al.") are used.

EXAMPLE 1

Preparation of Runaway Replication Plasmid from Plasmid R6K

Plasmid R6K is an *Escherichia coli* conjugative plasmid believed to be a narrow host range. Replication of R6K derivatives containing its oriV, called γ ori, generally requires a Rep protein, π(SEQ ID NO:2), which is encoded by the plasmid's pir gene. The π protein (SEQ ID NO:2) is bifunctional in replication; it acts as an activator of replication at low cellular levels and an inhibitor of replication at elevated levels. For a review of R6K replication and its control by π protein, see Filutowicz & Rakowski (1998) Gene 223, 195-204.

Using site-directed mutagenesis, the inventor has obtained the following three types of mutations within the pir gene (nucleotides 623-1540 of SEQ ID NO:1):

(1) double amino acid substitution: pro106leu, phe107ser (numbering of residues according to Stalker et al. (1982) J. Mol. Biol. 161:33-43).

(2) deletion of codons 106 and 107; and (3) deletion of codons 105, 106 and 107.

The γ ori was combined with the mutated pir genes in three configurations. In one configuration, the mutant gene was contained on a plasmid different from the plasmid containing the γ ori, thus providing π protein in trans. In another configuration, the mutant gene was integrated into the host chromosome, thus providing π protein also in trans. In third configuration the mutant pir gene was contained on the same plasmid with they ori, thus providing its function in cis.

EXAMPLE 2

Bacterial Cells Transformed with Plasmids Containing Mutated pir and ori in cis are Killed

*Escherichia coli* cells were transformed with either (1) the plasmids containing a mutated pir gene and the γ ori in trans; or (2) a plasmid containing a mutated pir gene and the γ ori in cis.

In transformed cells containing the mutant pir and the γ ori in trans, the copy number of the γ ori plasmid was increased 20- to 25-fold in comparison to wild-type pir controls. Cells transformed with the mutant pir and the γ on in cis were killed by the runaway replication of γ ori. The occurrence of the runaway phenotype when mutant pir is in cis to the ori but not in trans is believed to be caused by the enhanced effect of the origin activation and translation of nascent π protein occurring next to each other.

EXAMPLE 3

Preparation of Runaway Replication Plasmid from Plasmid RK2

Plasmid RK2 is a promiscuous plasmid that can replicate in 29 (and probably many more) gram-negative species (Guiney and Lanka, 1989, p 27-54. In C. M. Thomas (ed) Promiscous plasmids in gram-negative bacteria. London, Ltd London United Kingdom.). Plasmid RK2 is a 60-kb self-transmissible plasmid with a complete nucleotide sequence known (Pansegrau et al., 1994, J. Mol. Biol. 239, 623-663). A minimal replicon derived from this large plasmid has been obtained that is devoid of all its genes except for a trfA gene, that encodes plasmid's Rep protein called TrfA, and an origin of vegetative replication oriV For a review of RK2 replication and its control by TrfA protein, see Helinski et al., 1996 (In *Escherichia coli and Salmonella Cellular and Molecular Biology*, Vol. 2 (ed. F. Neidhardt, et al., 2295-2324, ASM Press, Washington D.C.). Combinations of specific mutations in the rep gene of plasmid RK2 (trfA) confer run-away replication on the minimal, self-replicating plasmid derivatives (Haugan et al., 1995, Plasmid 33, 27-39; Toukdarian and Helinski, 1998, Gene 223, 205-211). Such plasmids elicit a killing effect when introduced into wild type *E. coli* strains by transformation or electroporation. The inventors laboratory also constructed a plasmid which can inflict killing on bacterial host conditionally. This was achieved by using an inducible promoter which governs expression of a hyperactive version of trfA (trfA264 267); in the absence of an inducer, plasmid copy number is low (harmless) but in the presence of the inducer run-away replication occures, killing the host. The run-away plasmids, both constitutive and conditional, can be maintained in specially constructed strains in which a wild-type allele of the trfA gene (providing replication repressor) is also present, thereby suppressing over-replication (killing) by complementation. This and the previous examples illustrate not only the use of R6K derivatives to kill unwanted bacteria (Example 2 above) but also specifically constructed derivatives of other plasmids such as RK2.

The present invention is not limited to the embodiments described and exemplified above, but is capable of variation and modification without departure from the scope of the appended claims.

I claim:

1. A method of reducing or eliminating a target population of bacteria in a subject, the method comprising the step of:

administering to the subject donor bacterial cells harboring a transmissible plasmid that comprises a) an origin of replication for synthesizing the plasmid in a bacterial cell, wherein initiation of replication at the origin is negatively controlled by a plasmid replication protein comprising a copy number control function, wherein in the absence of the plasmid replication protein copy number control function, the transmissible plasmid undergoes runaway replication, b) a mutant gene encoding a plasmid replication protein comprising a copy number control function, wherein said mutant gene encoding said plasmid replication protein comprises a mutation that reduces the copy number control function of said plasmid replication protein, c) an origin of transfer from which conjugative transfer of the transmissible plasmid initiates from the donor bacterial cells to target bacterial cells, and d) at least one screenable marker gene, wherein each donor bacterial cell further comprises one or more transfer genes conferring upon the donor bacterial cell the ability to conjugatively transfer the transmissible plasmid to a target bacterial cell, wherein each donor bacterial cell further comprises a wild type gene encoding said plasmid replication protein comprising a copy number control function, wherein the target bacterial cells that do not produce the plasmid replication protein comprising a copy number control function, thereby enabling the transmissible plasmid to undergo runaway replication in the target bacterial cells, and wherein the donor bacterial cells are administered in a manner such that the donor bacterial cells contact the target bacterial cells and conjugatively transfer from the donor bacterial cells to the target bacterial cells, whereupon the transmissible plasmid undergoes runaway replication, thereby killing the target bacterial cells.

2. The method of claim 1, wherein the subject is a human or an animal.

3. The method of claim 1, wherein the subject is a plant.

4. The method of claim 1, wherein the subject is food or feed.

5. The method of claim 1, wherein a donor bacterial cell further comprises a helper plasmid, wherein said one or more transfer genes are contained on said helper plasmid, such that the transmissible plasmid is transmissible from the donor bacterial cell to a target bacterial cell, but is not further transmissible from the target bacterial cell to another target bacterial cell.

6. The method of claim 1, wherein said one or more transfer genes are contained on the transmissible plasmid, such that the transmissible plasmid is transmissible from the donor bacterial cell to a target bacterial cell, and further from the target bacterial cell to another target bacterial cell.

7. The method of claim 1, wherein said transfer genes are those of a plasmid selected from F, R6K and Ti.

8. The method of claim 1, wherein said plasmid replication protein is a bifunctional protein comprising a plasmid replication activator function and a plasmid replication inhibitor function, wherein when the plasmid replication activator function is present and when the plasmid replication inhibitor function is reduced, the transmissible plasmid undergoes runaway replication, and wherein said mutant gene encoding a plasmid replication protein comprising a copy number control function is a mutant gene encoding a bifunctional plasmid replication protein comprising a plasmid replication activator function and a plasmid replication inhibitor function, wherein said gene encoding said bifunctional plasmid replication protein comprises a mutation that reduces the plasmid replication inhibitor function of said bifunctional plasmid replication protein.

9. The method of claim 8, wherein said gene encoding said bifunctional protein comprises a pir gene from plasmid R6K, and wherein said pir gene encodes a π protein (SEQ ID NO:2).

10. The method of claim 8, wherein said gene encoding a mutant variant of said bifunctional protein comprises a mutant variant of a pir gene from plasmid R6K, and wherein said mutant variant of said bifunctional protein is a mutant variant of a non-mutant π protein (SEQ ID NO:2).

11. The method of claim 10, wherein said mutant variant of said π protein comprises at least one amino acid deletion or substitution relative to the amino acid sequence of said non-mutant π protein (SEQ ID NO:2).

12. The method of claim 11, wherein said at least one amino acid deletion or substitution comprises a deletion or substitution at amino acid 105, 106 or 107 of the amino acid sequence of said non-mutant π protein (SEQ ID NO:2).

13. The method of claim 11, wherein said at least one amino acid deletion or substitution comprises a deletion or substitution at amino acids 106 and 107 of the amino acid sequence of said non-mutant π protein (SEQ ID NO:2).

14. The method of claim 1, wherein the origin of replication is that of a plasmid selected from R6K, RK2, rts1, p15A and RSF1010.

15. The method of claim 1, wherein the origin of replication is selected from F and P1.

16. The method of claim 1, wherein the transmissible plasmid comprises a portion of a plasmid selected from RK2, R6K, pCU1, p15A, pIP501, pAMβ1 and pCRG1600.

17. The method of claim 1, wherein the donor bacterial cell is selected from dividing bacteria, maxicells, minicells and conditionally non-functional cells.

18. The method of claim 1, wherein the donor bacterial cell is selected from *Escherichia coli*, *Lactobacillus* spp., *Lactococcus*, *Bifidobacteria*, *Eubacteria*, and bacterial minicells.

19. The method of claim 1, wherein the target bacterial cell is selected from the group consisting of *Campylobacter* spp., *Enterobacter* spp., *Enterococcus* spp., *Escherichia coli*,

*Gardnerella vaginalis, Haemophilis* spp., *Helicobacter pylori, Mycobacterium tuberculosis, Propionobacter acnes, Pseudomonas aeruginosa* and other *Pseudomonas* spp., *Salmonella typhimurium, Shigella* spp. and *Staphylococcus* spp.

20. A method of reducing or eliminating a target population of bacteria in a subject, the method comprising:
    administering to the subject donor bacterial cells harboring a transmissible plasmid that comprises
    a) an origin of replication for synthesizing the plasmid in a bacterial cell, wherein initiation of replication at the origin is negatively controlled by a plasmid replication protein comprising a copy number control function, wherein in the absence of the plasmid replication protein copy number control function, the transmissible plasmid undergoes runaway replication,
    b) a mutant gene encoding a plasmid replication protein comprising a copy number control function, wherein said mutant gene encoding said plasmid replication protein comprises a mutation that reduces the copy number control function of said plasmid replication protein,
    c) an origin of transfer from which conjugative transfer of the transmissible plasmid initiates from the donor bacterial cells to target bacterial cells, and
    d) at least one screenable marker gene;
    wherein the transmissible plasmid is selected from the group consisting of R6K, RK2, pCU1, P15A, pIP501, pAMβ1 and pCRG1600;
    wherein each donor bacterial cell further comprises:
        i) one or more transfer genes conferring upon the donor bacterial cell the ability to conjugatively transfer the transmissible plasmid to a target bacterial cell, and
        ii) a wild type gene encoding said plasmid replication protein comprising a copy number control function,
    wherein the target bacterial cells do not produce the plasmid replication protein comprising a copy number control function, thereby enabling the transmissible plasmid to undergo runaway replication in the target bacterial cells, and
    wherein the donor bacterial cells are administered in a manner such that the donor bacterial cells contact the target bacterial cells and conjugatively transfer from the donor bacterial cells to the target bacterial cells, whereupon the transmissible plasmid undergoes runaway replication, thereby killing the target bacterial cells.

21. The method of claim 20 wherein the wherein the target bacterial cell is selected from the group consisting of *Campylobacter* spp., *Enterobacter* spp., *Enterococcus* spp., *Escherichia coli, Gardnerella vaginalis, Haemophilis* spp., *Helicobacter pylori, Mycobacterium tuberculosis, Propionobacter acnes, Pseudomonas aeruginosa* and other *Pseudomonas* spp., *Salmonella typhimurium, Shigella* spp. and *Staphylococcus* spp.

* * * * *

UNITED STATES PATENT AND TRADEMARK OFFICE
CERTIFICATE OF CORRECTION

PATENT NO. : 7,758,854 B2
APPLICATION NO. : 10/250645
DATED : July 20, 2010
INVENTOR(S) : Filutowicz It is certified that error appears in the above-identified patent and that said Letters Patent is hereby corrected as shown below:

Column 1, line 35 "cawing" should be "causing"
Column 5, line 8 "indueed" should be "induced"
Column 9, line 42 "fernentum" should "fermentum"
Column 11, line 9 "bacterial" should be "bacteria"
Column 12, line 63 "stain" should be "strain"

Signed and Sealed this

Fourteenth Day of September, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 2476
<212> TYPE: DNA
<213> ORGANISM: Escherichia coli
<220> FEATURE:
<221> NAME/KEY: misc_feature
<222> LOCATION: (1)..(2476)
<223> OTHER INFORMATION: Plasmid R6K
<220> FEATURE:
<221> NAME/KEY: CDS
<222> LOCATION: (623)..(1540)
<220> FEATURE:
<221> NAME/KEY: misc_feature
<222> LOCATION: (623)..(1540)
<223> OTHER INFORMATION: sequence for pir (pi) gene

<400> SEQUENCE: 1
gatcgctagt ttgttttgac tccatccatt agggcttcta aaacgccttc taaggccatg      60
tcagccgtta agtgttcctg tgtcactgaa aattgctttg agaggctcta agggcttctc     120
agtgcgttac atccctggct tgttgtccac aaccgttaaa ccttaaaagc tttaaaagcc     180
ttatatattc ttttttttct tataaaactt aaaaccttag aggctattta agttgctgat     240
ttatattaat tttattgttc aaacatgaga gcttagtacg tgaaacatga gagcttagta     300
cgttagccat gagagcttag tacgttagcc atgagggttt agttcgttaa acatgagagc     360
ttagtacgtt aaacatgaga gcttagtacg tgaaacatga gagcttagta cgtactatca     420
acaggttgaa ctgctgatct tcagatctag cttaaaacag gtggcttttt aatcatcttt     480
gccaagcatg gcgcgggttt ggggtaatat agcgactcat aaaagcgtta aacatgagtg     540
gatagtacgt tgctaaaaca tgagataaaa attgactctc atgttattgg cgttaagata     600
tacagaatga tgaggttttt tt atg aga ctc aag gtc atg atg gac gtg aac     652
                        Met Arg Leu Lys Val Met Met Asp Val Asn
                         1               5                  10 aaa aaa acg aaa att cgc cac cga aac gag cta aat cac acc ctg gct     700
Lys Lys Thr Lys Ile Arg His Arg Asn Glu Leu Asn His Thr Leu Ala
                15                  20                  25 caa ctt cct ttg ccc gca aag cga gtg atg tat atg gcg ctt gct ccc     748
Gln Leu Pro Leu Pro Ala Lys Arg Val Met Tyr Met Ala Leu Ala Pro
            30                  35                  40 att gat agc aaa gaa cct ctt gaa cga ggg cga gtt ttc aaa att agg     796
Ile Asp Ser Lys Glu Pro Leu Glu Arg Gly Arg Val Phe Lys Ile Arg
        45                  50                  55
```

-continued

| | | |
|---|---|---|
| gct gaa gac ctt gca gcg ctc gcc aaa atc acc cca tcg ctt gct tat<br>Ala Glu Asp Leu Ala Ala Leu Ala Lys Ile Thr Pro Ser Leu Ala Tyr<br>60                                 65                        70 | | 844 |
| cga caa tta aaa gag ggt ggt aaa tta ctt ggt gcc agc aaa att tcg<br>Arg Gln Leu Lys Glu Gly Gly Lys Leu Leu Gly Ala Ser Lys Ile Ser<br>75                            80                            85                        90 | | 892 |
| cta aga ggg gat gat atc att gct tta gct aaa gag ctt aac ctg ccc<br>Leu Arg Gly Asp Asp Ile Ile Ala Leu Ala Lys Glu Leu Asn Leu Pro<br>                                95                                    100                        105 | | 940 |
| ttt act gct aaa aac tcc cct gaa gag tta gat ctt aac att att gag<br>Phe Thr Ala Lys Asn Ser Pro Glu Glu Leu Asp Leu Asn Ile Ile Glu<br>                           110                              115                            120 | | 988 |
| tgg ata gct tat tca aat gat gaa gga tac ttg tct tta aaa ttc acc<br>Trp Ile Ala Tyr Ser Asn Asp Glu Gly Tyr Leu Ser Leu Lys Phe Thr<br>                    125                              130                            135 | | 1036 |
| aga acc ata gaa cca tat atc tct agc ctt att ggg aaa aaa aat aaa<br>Arg Thr Ile Glu Pro Tyr Ile Ser Ser Leu Ile Gly Lys Lys Asn Lys<br>        140                              145                              150 | | 1084 |
| ttc aca acg caa ttg tta acg gca agc tta cgc tta agt agc cag tat<br>Phe Thr Thr Gln Leu Leu Thr Ala Ser Leu Arg Leu Ser Ser Gln Tyr<br>155                               160                              165                        170 | | 1132 |
| tca tct tct ctt tat caa ctt atc agg aag cat tac tct aat ttt aag<br>Ser Ser Ser Leu Tyr Gln Leu Ile Arg Lys His Tyr Ser Asn Phe Lys<br>                           175                              180                            185 | | 1180 |
| aag aaa aat tat ttt att att tcc gtt gat gag tta aag gaa gag tta<br>Lys Lys Asn Tyr Phe Ile Ile Ser Val Asp Glu Leu Lys Glu Glu Leu<br>                    190                              195                            200 | | 1228 |
| aca gct tat act ttt gat aaa gat gga aat att gag tac aaa tac cct<br>Thr Ala Tyr Thr Phe Asp Lys Asp Gly Asn Ile Glu Tyr Lys Tyr Pro<br>                    205                              210                            215 | | 1276 |
| gac ttt cct att ttt aaa agg gat gtg tta aat aaa gcc att gct gaa<br>Asp Phe Pro Ile Phe Lys Arg Asp Val Leu Asn Lys Ala Ile Ala Glu<br>220                               225                              230 | | 1324 |
| att aaa aag aaa aca gaa ata tcg ttt gtt ggc ttc act gtt cat gaa<br>Ile Lys Lys Lys Thr Glu Ile Ser Phe Val Gly Phe Thr Val His Glu<br>235                               240                            245                        250 | | 1372 |
| aaa gaa gga aga aaa att agt aag ctg aag ttc gaa ttt gtc gtt gat<br>Lys Glu Gly Arg Lys Ile Ser Lys Leu Lys Phe Glu Phe Val Val Asp<br>                    255                              260                            265 | | 1420 |
| gaa gat gaa ttt tct ggc gat aaa gat gat gaa gct ttt ttt atg aat<br>Glu Asp Glu Phe Ser Gly Asp Lys Asp Asp Glu Ala Phe Phe Met Asn<br>                           270                              275                            280 | | 1468 |
| tta tct gaa gct gat gca gct ttt ctc aag gta ttt gat gaa acc gta<br>Leu Ser Glu Ala Asp Ala Ala Phe Leu Lys Val Phe Asp Glu Thr Val<br>                  285                              290                            295 | | 1516 |
| cct ccc aaa aaa gct aag ggg tga tatatggcta aaatttacga tttccctcaa<br>Pro Pro Lys Lys Ala Lys Gly<br>300                             305 | | 1570 |
| ggagccgaac gccgcaggat gcaccgcaaa atccagtgga caacgctgt aaaattatct | | 1630 |
| aaaaatggct ggagtaagcc agaggttaaa cgctggtctt ttttagcatt catctcaact | | 1690 |
| ggctggtatt actttcgcct ttcggtagca gtcattttcc atatcattac tatttgtggt | | 1750 |
| ttagctgtgc tcgcggcgtt aagcaatacg atattctgga ttggtggcgc gatatgtctt | | 1810 |
| gtaacctggt atacaaatga ccatcaaatt tggagtacta acaatcttac tatccctatt | | 1870 |
| gttttcggac tttgggtgtt aagtttagta gctgcaccac tcatagattt tttcagtcaa | | 1930 |
| aaattgccct tttatcgtct tcttgtgcct gatgcgaagc gtgaggaagt gggcgaagat | | 1990 |
| gattcttaaa gccctgccct gtacggcttt aacgccttct cgcggtagat ctatggatgt | | 2050 |

-continued

```
tgagaatgta gtatggttat actgcgatgc aggatagggc aaacgccgta aaatgacgtc    2110
tttgacgtta tttttcagcg cttgcccggt gacctacagt cggtgcttgt tgggagattt    2170
tatgaagttt actagtaaag gattttatca gtgataaata tgcaaaggct attaacattt    2230
taaatgataa ccttaaagaa aactactatg tttttatgg tgtaaggtta agtgaaattc     2290
tttttcctgc aagtgattat ggtacagatg attttttaa ggagtttgag gaaataaaca    2350
acgttacctt gcctttagtt gtttttgaaa taaatgaacg tgaacctgtg attgtaattg    2410
gttttgatga aataaatcct gcgattctta tagagaaatc cggtataaag gttttagtaa    2470
tcggac                                                              2476
```

<210> SEQ ID NO 2
<211> LENGTH: 305
<212> TYPE: PRT
<213> ORGANISM: Escherichia coli

<400> SEQUENCE: 2

```
Met Arg Leu Lys Val Met Met Asp Val Asn Lys Lys Thr Lys Ile Arg
1               5                   10                  15

His Arg Asn Glu Leu Asn His Thr Leu Ala Gln Leu Pro Leu Pro Ala
            20                  25                  30

Lys Arg Val Met Tyr Met Ala Leu Ala Pro Ile Asp Ser Lys Glu Pro
        35                  40                  45

Leu Glu Arg Gly Arg Val Phe Lys Ile Arg Ala Glu Asp Leu Ala Ala
    50                  55                  60

Leu Ala Lys Ile Thr Pro Ser Leu Ala Tyr Arg Gln Leu Lys Glu Gly
65                  70                  75                  80

Gly Lys Leu Leu Gly Ala Ser Lys Ile Ser Leu Arg Gly Asp Asp Ile
                85                  90                  95

Ile Ala Leu Ala Lys Glu Leu Asn Leu Pro Phe Thr Ala Lys Asn Ser
            100                 105                 110

Pro Glu Glu Leu Asp Leu Asn Ile Ile Glu Trp Ile Ala Tyr Ser Asn
        115                 120                 125

Asp Glu Gly Tyr Leu Ser Leu Lys Phe Thr Arg Thr Ile Glu Pro Tyr
    130                 135                 140

Ile Ser Ser Leu Ile Gly Lys Lys Asn Lys Phe Thr Thr Gln Leu Leu
145                 150                 155                 160

Thr Ala Ser Leu Arg Leu Ser Ser Gln Tyr Ser Ser Ser Leu Tyr Gln
                165                 170                 175

Leu Ile Arg Lys His Tyr Ser Asn Phe Lys Lys Asn Tyr Phe Ile
            180                 185                 190

Ile Ser Val Asp Glu Leu Lys Glu Glu Leu Thr Ala Tyr Thr Phe Asp
        195                 200                 205

Lys Asp Gly Asn Ile Glu Tyr Lys Tyr Pro Asp Phe Pro Ile Phe Lys
    210                 215                 220

Arg Asp Val Leu Asn Lys Ala Ile Ala Glu Ile Lys Lys Thr Glu
225                 230                 235                 240

Ile Ser Phe Val Gly Phe Thr Val His Glu Lys Glu Gly Arg Lys Ile
                245                 250                 255

Ser Lys Leu Lys Phe Glu Phe Val Asp Glu Asp Glu Phe Ser Gly
            260                 265                 270

Asp Lys Asp Asp Glu Ala Phe Phe Met Asn Leu Ser Glu Ala Asp Ala
    275                 280                 285
```

-continued

```
Ala Phe Leu Lys Val Phe Asp Glu Thr Val Pro Pro Lys Lys Ala Lys
    290                 295                 300
Gly
305
```